United States Patent
Cao et al.

(10) Patent No.: US 9,597,525 B2
(45) Date of Patent: Mar. 21, 2017

(54) T-WAVE OVERSENSING REJECTION

(71) Applicant: Medtronic, Inc., Minneapolis, MN (US)

(72) Inventors: Jian Cao, Shoreview, MN (US); Xusheng Zhang, Shoreview, CA (US); Robert W. Stadler, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/705,010

(22) Filed: May 6, 2015

(65) Prior Publication Data
US 2016/0325106 A1 Nov. 10, 2016

(51) Int. Cl.
*A61N 1/00* (2006.01)
*A61N 1/39* (2006.01)
*A61B 5/0452* (2006.01)
*A61B 5/04* (2006.01)

(52) U.S. Cl.
CPC ........ *A61N 1/3987* (2013.01); *A61B 5/04012* (2013.01); *A61B 5/0452* (2013.01); *A61N 1/3925* (2013.01)

(58) Field of Classification Search
CPC .. A61B 5/04012; A61B 5/0452; A61N 1/3925
See application file for complete search history.

(56) References Cited

U.S. PATENT DOCUMENTS

| | | | |
|---|---|---|---|
| 5,683,426 A | 11/1997 | Greenhut et al. | |
| 7,333,855 B2 | 2/2008 | Gunderson et al. | |
| 7,567,835 B2 | 7/2009 | Gunderson et al. | |
| 7,734,333 B2 | 6/2010 | Ghanem et al. | |
| 7,783,354 B2 | 8/2010 | Gunderson | |
| 7,813,791 B1 | 10/2010 | Gill et al. | |
| 7,831,304 B2 | 11/2010 | Cao et al. | |
| 8,160,684 B2 | 4/2012 | Ghanem et al. | |
| 8,260,404 B1 | 9/2012 | Bharmi et al. | |
| 8,265,737 B2 | 9/2012 | Warren et al. | |
| 8,386,024 B2 | 2/2013 | Gunderson et al. | |
| 8,437,842 B2 | 5/2013 | Zhang et al. | |
| 8,504,144 B2 | 8/2013 | Bharmi et al. | |
| 8,538,524 B2 | 9/2013 | Rosenberg et al. | |
| 8,548,573 B2 | 10/2013 | Keefe | |
| 8,583,221 B1 | 11/2013 | Patel et al. | |
| 8,886,296 B2 | 11/2014 | Patel | |
| 8,914,106 B2 | 12/2014 | Charlton et al. | |
| 8,929,977 B2 | 1/2015 | Allavatam et al. | |

(Continued)

OTHER PUBLICATIONS (PCT/US2016/030512) Communication Relating to the Results of the Partial International Search, Mailed Sep. 13, 2016, 8 pages.

(Continued)

*Primary Examiner* — Robert N Wieland

(57) ABSTRACT

A medical device coupled to extracardiac electrodes is configured to analyze a cardiac electrical signal over a signal analysis segment to determine if shockable rhythm classification criteria are met, determine that TWOS detection criteria are met for the signal analysis segment when a predetermined number of TWOS analysis windows are classified as TWOS, and classify the signal analysis segment as non-shockable in response to determining that the TWOS detection criteria are met.

18 Claims, 7 Drawing Sheets

(56) References Cited

U.S. PATENT DOCUMENTS

| | | |
|---|---|---|
| 8,942,795 B2 | 1/2015 | Gunderson et al. |
| 2008/0082014 A1* | 4/2008 | Cao ................... A61B 5/0452 600/509 |
| 2009/0018595 A1 | 1/2009 | Bharmi et al. |
| 2011/0098764 A1 | 4/2011 | Sloman et al. |
| 2013/0060117 A1 | 3/2013 | Gunderson et al. |
| 2013/0096449 A1 | 4/2013 | Patel et al. |
| 2014/0277221 A1 | 9/2014 | Charlton et al. |

OTHER PUBLICATIONS (PCT/US2016/030512) PCT Notification of Transmittal of the International Search Report and the Written Opinion of the International Searching Authority, Mailed Nov. 17, 2016, 18 pages.

* cited by examiner

T-WAVE OVERSENSING REJECTION

TECHNICAL FIELD

The disclosure relates generally to implantable medical devices and, in particular, to a method and apparatus for rejecting time segments including T-wave oversensing to avoid false cardiac tachyarrhythmia detection, particularly in extracardiac implantable medical systems.

BACKGROUND

A variety of implantable medical devices (IMDs) for delivering a therapy, monitoring a physiological condition of a patient or a combination thereof have been clinically implanted or proposed for clinical implantation in patients. Some IMDs may employ one or more elongated electrical leads carrying stimulation electrodes, sense electrodes, and/or other sensors. IMDs may deliver therapy to or monitor conditions of a variety of organs, nerves, muscle or tissue, such as the heart, brain, stomach, spinal cord, pelvic floor, or the like. Implantable medical leads may be configured to allow electrodes or other sensors to be positioned at desired locations for delivery of electrical stimulation or sensing of physiological conditions. For example, electrodes or sensors may be carried along a distal portion of a lead. A proximal portion of the lead may be coupled to an implantable medical device housing, which may contain circuitry such as signal generation circuitry and/or sensing circuitry.

Some IMDs, such as cardiac pacemakers or implantable cardioverter defibrillators (ICDs), provide therapeutic electrical stimulation to the heart of the patient via electrodes carried by one or more implantable leads. The leads may be transvenous, e.g., implanted in the heart through one or more veins. Other leads may be non-transvenous leads implanted outside the heart, e.g., implanted epicardially, pericardially, or subcutaneously. In either case, the electrical stimulation provided by the IMD may include signals such as pacing pulses, cardioversion shocks or defibrillation shocks to address abnormal cardiac rhythms such as bradycardia, tachycardia or fibrillation.

IMDs capable of delivering electrical stimulation for treating abnormal cardiac rhythms typically sense signals representative of intrinsic depolarizations of the heart and analyze the sensed signals to identify the abnormal rhythms. Upon detection of an abnormal rhythm, the device may deliver an appropriate electrical stimulation therapy to restore a more normal rhythm. For example, an IMD may deliver pacing pulses to the heart upon detecting tachycardia or bradycardia, and deliver cardioversion or defibrillation shocks to the heart upon detecting tachycardia or fibrillation. In some instances, cardiac signals may be oversensed or undersensed. Oversensing and undersensing interferes with the proper detection of the abnormal rhythms. For example, oversensing of cardiac electrical signals can lead to the false detection of a pathologically fast heart rate, potentially resulting in an electrical stimulation therapy that is not needed.

SUMMARY

In general, the disclosure is directed to techniques for detecting T-wave oversensing (TWOS) to avoid delivery of unnecessary cardioversion/defibrillation (CV/DF) shocks. An implantable cardioverter defibrillator (ICD), such as an ICD coupled to a non-transvenous, subcutaneous lead, operating in accordance with the techniques of this disclosure acquires cardiac electrical signals using extracardiac electrodes and analyzes groups of cardiac events sensed from the acquired cardiac electrical signals for detecting TWOS.

In one example, the disclosure provides a method performed by a medical device, including receiving a cardiac electrical signal from a patient's heart via extracardiac electrodes coupled to the medical device, setting a signal analysis segment of the cardiac electrical signal, analyzing the signal analysis segment to determine if shockable rhythm classification criteria are met for the signal analysis segment, setting TWOS analysis windows, analyzing cardiac events of the cardiac electrical signal to classify each TWOS analysis window of the plurality of TWOS analysis windows as one of TWOS and no TWOS, determining that TWOS detection criteria are met for the signal analysis segment when a predetermined number of the TWOS analysis windows are classified as TWOS, and classifying the signal analysis segment as non-shockable in response to determining that the TWOS detection criteria are met.

In another example, the disclosure provides an implantable medical device including a sensing module configured to receive a cardiac electrical signal via extracardiac electrodes coupled to the implantable medical device and a control module coupled to the sensing module. The control module is configured to set a signal analysis segment of the cardiac electrical signal, analyze the signal analysis segment to determine if shockable rhythm classification criteria are met for the signal analysis segment, set TWOS analysis windows, analyze cardiac events of the cardiac electrical signal to classify each TWOS analysis window of the plurality of TWOS analysis windows as one of TWOS and no TWOS, determine that TWOS detection criteria are met for the signal analysis segment when a predetermined number of the TWOS analysis windows are classified as TWOS, and classify the signal analysis segment as non-shockable in response to determining that the TWOS detection criteria are met.

In another example, the disclosure provides a non-transitory, computer-readable storage medium comprising a set of instructions which, when executed by a control module of a medical device, cause the medical device to receive a cardiac electrical signal from a patient's heart via a plurality of extracardiac electrodes coupled to the medical device, set a signal analysis segment of the cardiac electrical signal, analyze the signal analysis segment to determine if shockable rhythm classification criteria are met for the signal analysis segment, set TWOS analysis windows, analyze cardiac events of the cardiac electrical signal to classify each TWOS analysis window of the plurality of TWOS analysis windows as one of TWOS and no TWOS, determine that TWOS detection criteria are met for the signal analysis segment when a predetermined number of the TWOS analysis windows are classified as TWOS, and classify the signal analysis segment as non-shockable in response to determining that the TWOS detection criteria are met.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

In general, this disclosure describes techniques for detecting TWOS. Detection of TWOS is used to reject time segments of a cardiac electrical signal that have been classified as shockable cardiac rhythm segments based on rate and/or morphology tachyarrhythmia detection criteria. As used herein, a "shockable cardiac rhythm" is a ventricular tachyarrhythmia, such as ventricular fibrillation (VF), that poses danger to the patient such that a CV/DF shock therapy is needed in order to ensure the safety of the patient. CV/DF shocks may be delivered to one or both of the ventricles. TWOS can lead to detection of a fast heart rate and false detection of a shockable rhythm resulting in an unnecessary CV/DF shock. CV/DF shocks are painful but, when appropriate, can be lifesaving for the patient. TWOS detection can reduce the incidence of unnecessary CV/DF shocks delivered due to false shockable rhythm detection.

Figure 1:
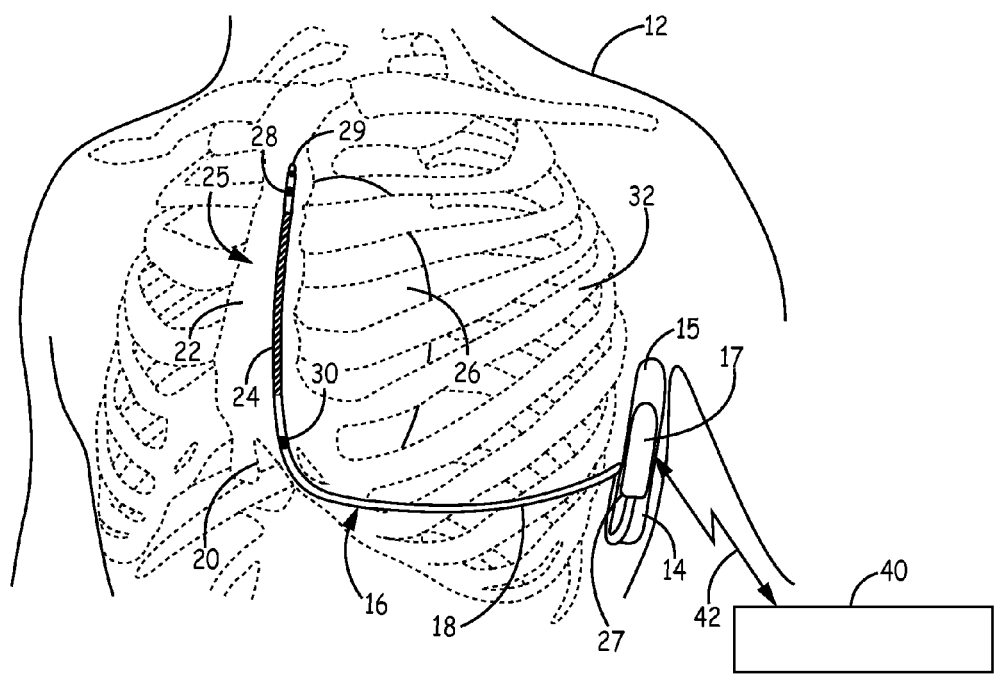
FIG. 1 is a conceptual diagram of a patient implanted with an example IMD system that includes an ICD coupled to a defibrillation lead.

FIG. 1 is a conceptual diagram of a patient 12 implanted with an example extravascular IMD system 10 that includes a subcutaneously implanted ICD 14 coupled to an extravascular defibrillation lead 16. As used herein, the term "extravascular" refers to a position outside the blood vessels, heart 26 and the pericardium surrounding heart 26 of patient 12.

ICD 14 includes a housing 15 and connector assembly 17. ICD 14 is configured to detect shockable rhythms and deliver a CV/DF shock therapy via extracardiac electrodes carried by lead 16. ICD 14 acquires cardiac electrical signals, i.e., electrocardiogram (ECG) signals, using extracardiac electrodes carried by defibrillation lead 16 and housing 15. As will be described herein, the ECG signals are analyzed for detecting TWOS. ECG signals are also analyzed for classifying ECG signal segments as shockable or non-shockable. Detection of TWOS precludes classification of an ECG signal segment as shockable, reducing the likelihood of delivering an unnecessary shock therapy due to TWOS.

Defibrillation lead 16 includes a proximal end 27 that is connected to ICD 14 and a distal portion 25 that carries electrodes 24, 28 and 30. Electrode 24 is a defibrillation electrode used with the conductive housing 15 of ICD 14 as an indifferent, return electrode to deliver high voltage CV/DF shocks. All or a portion of housing 15 of ICD 14 may be formed of a conductive material, such as titanium or titanium alloy, and coupled to internal ICD circuitry to function as an electrode, sometimes referred to as a "CAN electrode." A shock vector pathway extends from defibrillation electrode 24 to housing 15, through the ventricular myocardium. Defibrillation electrode 24 is typically an elongated coil electrode having a relatively higher surface area than electrode 28 and 30 for delivering the high voltage shock, but may be implemented as another type of electrode other than a coil electrode.

Electrodes 28 and 30 are referred to herein as sensing electrodes because they may be used for sensing ECG signals. An ECG signal may be sensed using any combination of electrodes 28, 30 and housing 15. For example a sensing vector between electrodes 28 and 30, a sensing vector between electrode 28 and housing 15 or a sensing vector between electrode 30 and housing 15 may be chosen. In some examples, a sensing vector may even include defibrillation electrode 24. As described below, sensing vectors may be selected two at a time by ICD 14 for monitoring for a shockable rhythm and for detecting TWOS. While three electrodes 24, 28 and 30 are shown along lead 16, lead 16 may carry more or fewer electrodes in other examples. In the example illustrated in FIG. 1, sensing electrodes 28 and 30 are separated from one another by defibrillation electrode 24. In other words, sensing electrode 28 is located distal to defibrillation electrode 24, and sensing electrode 30 is proximal to defibrillation electrode 24. In various examples, electrodes 28 and 30 may be carried along lead 16 at other locations than those shown but are generally positioned to acquire ECG signals having acceptable cardiac signal strength for sensing cardiac events, such as R-wave signals that occur upon depolarization of the ventricles.

It is understood that one or more leads may be coupled to ICD 14 for connecting at least one defibrillation electrode and one sensing electrode to ICD 14 for monitoring cardiac electrical signals and delivering CV/DF shock therapy. Furthermore, it is recognized that, even though electrode 24 is referred to herein as a "defibrillation electrode" and that electrodes 28 and 30 are referred to herein as "sensing electrodes," any of electrodes 24, 28 and 30 and housing 15 electrically coupled to a therapy delivery module of ICD 14 may be used for delivering cardiac pacing pulses to restore a more normal heart rhythm in some examples. Pacing therapies that may be delivered by ICD 14 using any of electrodes 24, 28, 30 and housing 15 may include anti-tachycardia pacing (ATP) and/or post-shock pacing for treating bradycardia or asystole after a CV/DF shock.

Defibrillation lead 16 is illustrated in FIG. 1 as being implanted subcutaneously or submuscularly, between the skin and the ribcage 32 and/or sternum 22. ICD 14 is shown implanted near a midaxillary line of patient 12. In this position, defibrillation lead 16 extends subcutaneously from ICD 14 toward xiphoid process 20. At a location near xiphoid process 20 defibrillation lead 16 bends or turns and extends subcutaneously superior, substantially parallel to sternum 22. The distal portion 25 of defibrillation lead 16 may be parallel over sternum 22 or laterally offset from sternum 22, to the left or the right. In other examples, the distal end 29 of defibrillation lead 16 may be angled laterally away from sternum 22 either to the left or the right such that the distal portion 25 extends non-parallel to sternum 22.

Figure 2:
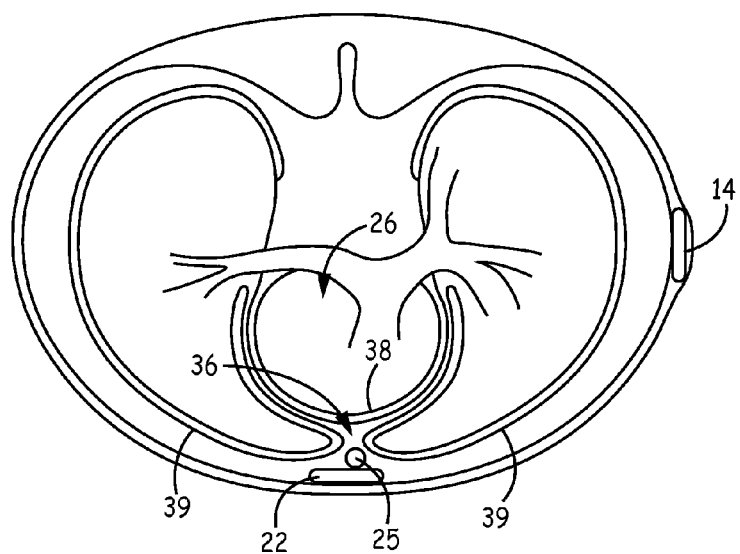
FIG. 2 is a transvers view of the patient of FIG. 1 showing an alternate implant location of the defibrillation lead of FIG. 1.

In other instances, lead 16 may be implanted at other extravascular locations. As shown in a transverse view of patient 12 in FIG. 2, lead 16 may be implanted at least partially in a substernal location, e.g., between the ribcage 32 and/or sternum 22 and heart 26. In one such configuration, a proximal portion (not seen in the transverse view of FIG. 2) of lead 16 extends subcutaneously from ICD 14 toward sternum 22 and a distal portion 25 of lead 16 extends superior under or below the sternum 22 in the anterior mediastinum 36. Anterior mediastinum 36 is bounded laterally by pleurae 39, posteriorly by pericardium 38, and anteriorly by sternum 22.

In some instances, the anterior wall of anterior mediastinum 36 may also be formed by the transversus thoracis and one or more costal cartilages. Anterior mediastinum 36 includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 16 extends along the posterior side of sternum 22 substantially within the loose connective tissue and/or substernal musculature of anterior mediastinum 36. Lead 16 may be at least partially implanted in other intrathoracic locations, e.g., other non-vascular, extra-pericardial locations, including the gap, tissue, or other anatomical features around the perimeter of and adjacent to, but not attached to, the pericardium or other portion of heart 26.

ICD 14 may also be implanted at other subcutaneous locations on patient 12, such as further posterior on the torso toward the posterior axillary line, further anterior on the torso toward the anterior axillary line, in a pectoral region, or at other locations of patient 12. In instances in which ICD 14 is implanted pectorally, lead 16 would follow a different path, e.g., across the upper chest area and inferior along sternum 22. When the ICD 14 is implanted in the pectoral region, the system 10 may include a second lead including a defibrillation electrode that extends along the left side of the patient such that the defibrillation electrode of the second lead is located along the left side of the patient to function as an anode or cathode of a therapy vector including another defibrillation electrode located anteriorly for defibrillating heart 26 positioned there between.

In another example, ICD 14 may be implanted subcutaneously outside the ribcage 32 in an anterior medial location. Lead 16 may be tunneled subcutaneously into a location adjacent to a portion of the latissimus dorsi muscle of patient 12, from a medial implant pocket of ICD 14 laterally and posteriorly to the patient's back to a location opposite heart 26 such that the heart 26 is generally disposed between the ICD 14 and defibrillation electrode 24 and distal sensing electrode 28.

Referring again to FIG. 1, lead 16 includes an elongated lead body 18 carrying electrodes 24, 28 and 30 located along the distal portion 25 of the length of the lead body 18. Lead body 18 insulates one or more elongated electrical conductors (not illustrated) that extend from a respective electrode 24, 28 and 30 through the lead body 18 to a proximal connector (not shown) that is coupled to ICD 14 at lead proximal end 27. Lead body 18 may be formed from a non-conductive material, such as silicone, polyurethane, fluoropolymers, or mixtures thereof or other appropriate materials, and is shaped to form one or more lumens within which the one or more conductors extend. The conductors are electrically coupled to ICD circuitry, such as a therapy delivery module or a sensing module, via connections in ICD connector assembly 17 that includes a connector bore for receiving the proximal connector of lead 16 and associated electrical feedthroughs crossing ICD housing 15. The electrical conductors transmit electrical stimulation therapy from a therapy module within ICD 14 to one or more of electrodes 24, 28, and 30, and transmit cardiac electrical signals from one or more of electrodes 24, 28, and 30 to the sensing module within ICD 14.

Housing 15 forms a hermetic seal that protects internal electronic components of ICD 14. As indicated above, housing 15 may function as a "CAN electrode" since the conductive housing or a portion thereof may be electrically coupled to internal circuitry to be used as an indifferent or ground electrode during ECG sensing or during cardioversion/defibrillation shock delivery. ICD 14 also includes connector assembly 17 (sometimes referred to as a connector block or header) that includes electrical feedthroughs through which electrical connections are made between electrical conductors within lead 16 and electronic components included within the housing 15. As will be described in further detail herein, housing 15 may enclose one or more processors, memory devices, transmitters, receivers, sensors, sensing circuitry, therapy circuitry and other appropriate components.

The example illustrated in FIG. 1 is illustrative in nature and should not be considered limiting of the techniques described in this disclosure. The techniques disclosed herein may be implemented in numerous ICD and electrode configurations that include extracardiac electrodes for sensing cardiac electrical signals for detecting shockable rhythms. As used herein, "extracardiac" electrodes are electrodes that are located outside of heart 26 and pericardium 38 and have no direct contact with heart 26. The IMD system 10 is referred to as an extravascular or extracardiac IMD system because lead 16 is a non-transvenous lead, positioned in an extravascular location outside the blood vessels, heart 26 and pericardium 38, carrying extracardiac electrodes.

An external device 40 is shown in telemetric communication with ICD 14 by a communication link 42. External device may include a processor, display, user interface, telemetry unit and other components for communicating with ICD 14 for transmitting and receiving data via communication link 42. Communication link 42 may be established between ICD 14 and external device 40 using a radio frequency (RF) link such as Bluetooth, Wi-Fi, or Medical Implant Communication Service (MICS) or other RF bandwidth. External device 40 may be embodied as a programmer used in a hospital, clinic or physician's office to retrieve data from ICD 14 and to program operating parameters and algorithms in ICD 14 for controlling ICD functions. External device 40 may be used to program shockable rhythm detection parameters and CV/DF shock therapy control parameters used by ICD 14. Data stored or acquired by ICD 14, including physiological signals or associated data derived therefrom, results of device diagnostics, and histories of detected shockable rhythm episodes and delivered therapies, may be retrieved from ICD 14 by external device 40 following an interrogation command. External device 40 may alternatively be embodied as a home monitor or hand held device.

Figure 3:
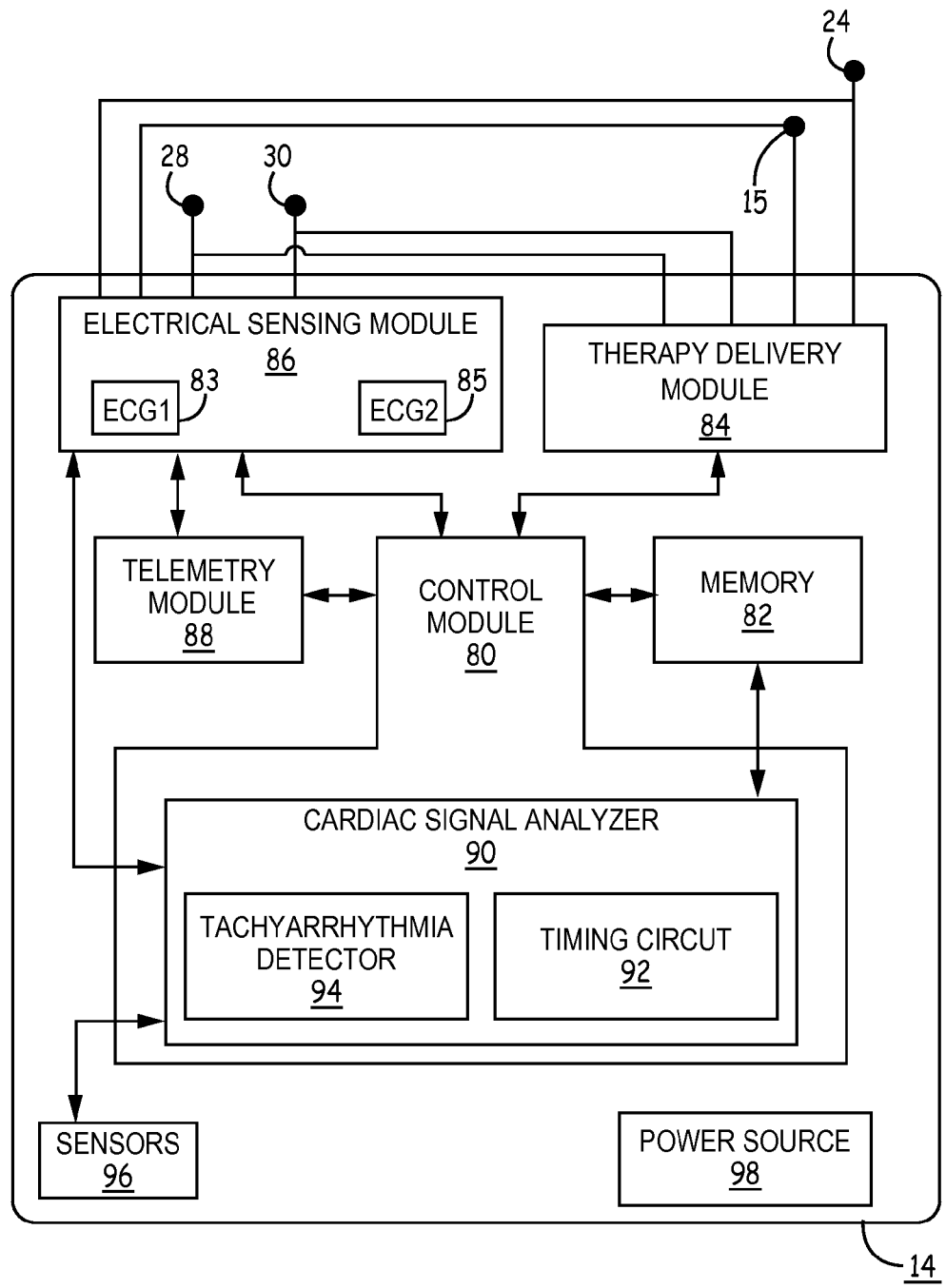
FIG. 3 is a schematic diagram of the ICD of FIG. 1 according to one example.

FIG. 3 is a schematic diagram of ICD 14 according to one example. The electronic circuitry enclosed within housing 15 includes software, firmware and hardware that cooperatively monitor one or more ECG signals, determine when a CV/DF shock is necessary, and deliver prescribed CV/DF shock therapies. ICD 14 may be coupled to a lead, such as lead 16 shown in FIG. 1, carrying extracardiac electrodes 24, 28 and 30, positioned in operative relation to the patient's heart (but outside of the heart) for delivering shock therapies and sensing cardiac electrical signals.

ICD 14 includes a control module 80, memory 82, therapy delivery module 84, electrical sensing module 86, and telemetry module 88. Control module 80 includes a cardiac signal analyzer 90 including a tachyarrhythmia detector 94 and timing circuit 92. A power source 98 provides power to the circuitry of ICD 14, including each of the modules 80, 84, 86, 88, 90 and memory 82 as needed. Power source 98 may include one or more energy storage devices, such as one or more rechargeable or non-rechargeable batteries.

The functional blocks shown in FIG. 3 represent functionality included in ICD 14 and may include any discrete and/or integrated electronic circuit components that implement analog and/or digital circuits capable of producing the functions attributed to ICD 14 herein. For example, the modules may include analog circuits, e.g., amplification circuits, filtering circuits, and/or other signal conditioning circuits. The modules may also include digital circuits, e.g., analog-to-digital converters, digital signal processors (DSPs), combinational or sequential logic circuits, integrated circuits, application specific integrated circuit (ASIC), memory devices, etc. As used herein, the term "module" refers to an ASIC, an electronic circuit, a processor (shared, dedicated, or group) and memory that execute one or more software or firmware programs, a combinational logic circuit, state machine, or other suitable components that provide the described functionality. The particular form of software, hardware and/or firmware employed to implement the functionality disclosed herein will be determined primarily by the particular system architecture employed in the device and by the particular detection and therapy delivery methodologies employed by the ICD. Providing software, hardware, and/or firmware to accomplish the described functionality in the context of any modern IMD system, given the disclosure herein, is within the abilities of one of skill in the art.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control module 80 or other ICD modules to perform various functions attributed to ICD 14. The non-transitory computer readable media storing the instructions may include any of the media listed above, with the sole exception being a transitory propagating signal.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common hardware or software components. For example, shockable rhythm detection operations performed by cardiac signal analyzer 90 for determining a need for therapy delivered by ICD 14 may be implemented in control module 80 executing instructions stored in memory 82.

Control module 80 communicates with therapy delivery module 84 and electrical sensing module 86 for sensing cardiac electrical activity, detecting cardiac rhythms, and controlling delivery of cardiac therapies in response to sensed cardiac signals. Therapy delivery module 84 and electrical sensing module 86 are electrically coupled to electrodes 24, 28, and 30 carried by lead 16 (shown in FIG. 1) and the housing 15, which may function as a sensing electrode or a common or ground electrode during shock therapy delivery.

Electrical sensing module 86 is selectively coupled to electrodes 28, 30 and housing 15 in order to monitor electrical activity of the patient's heart. Electrical sensing module 86 may additionally be selectively coupled to electrode 24. Sensing module 86 is enabled to selectively monitor one or more physical sensing vectors selected from the available electrodes 24, 28, 30 and 15. For example, sensing module 86 may include switching circuitry for selecting which of electrodes 24, 28, 30 and housing 15 are coupled to sense amplifiers or other cardiac event detection circuitry included in sensing module 86. Switching circuitry may include a switch array, switch matrix, multiplexer, or any other type of switching device suitable to selectively couple sense amplifiers to selected electrodes.

In some examples, electrical sensing module 86 includes multiple sensing channels 83 and 85 for sensing multiple ECG sensing vectors selected from electrodes 24, 28, 30 and housing 15. Sensing module 86 is shown to include two sensing channels 83 and 85 in the example of FIG. 3. Each sensing channel 83 and 85 may be configured to amplify, filter and rectify the ECG signal received from selected electrodes coupled to the respective sensing channel to improve the signal quality for sensing cardiac events, e.g., R-waves.

In one example, a first sensing channel 83 (ECG1) may be selectably configured to sense an ECG signal between sensing electrode 30 and ICD housing 15 and the second sensing channel 85 (ECG2) may be selectably configured to sense an ECG signal using electrodes 28 and 30. The sensing module 84 may alternatively be selectively configured to sense a cardiac electrical signal between sensing electrode 28 and ICD housing 15. In other examples, one sensing channel 83 or 85 may receive an ECG signal using defibrillation electrode 24.

Each sensing channel 83 and 85 includes cardiac event detection circuitry for sensing cardiac events from the received ECG signal developed across the selected electrodes 24, 28, 30 or 15. Cardiac event sensing thresholds used by each sensing channel 83 and 85 may be automatically adjusted according to sensing control parameters, which may be stored in memory 82. Each sensing channel 83 and 85 senses a cardiac event when the respectively received ECG signal crosses the auto-adjusting cardiac event sensing threshold. For example, an R-wave sensing threshold used to sense ventricular events from a rectified ECG signal may be set to 60% of the peak amplitude of the currently sensed event. The auto-adjusting sensing threshold may decay from the starting threshold to a floor threshold until the next ventricular event is sensed (or a pacing escape interval expires).

Each time the received ECG signal crosses the sensing threshold for a given channel 83 or 85 outside a blanking interval, a cardiac event sense signal, also referred to herein as a "sense event signal" such as an "ventricular sense event signal," is produced and passed to control module 80. For example, ventricular sense event signals may be passed to tachyarrhythmia detector 94 and timing circuit 92 of cardiac signal analyzer 90 when a received ECG signal crosses the R-wave sensing threshold for a given channel 83 or 85. Sense event signals produced by sensing channel 83 or 85 may be used in detecting a shockable rhythm based on event intervals meeting VT or VF detection criteria and for scheduling R-wave synchronized shocks by timing circuit 92.

Sensing module 86 may include an analog-to-digital converter for providing a digitized ECG vector signal from one or both sensing channels 83 and 85 to control module 80 and/or cardiac signal analyzer 90. For example an ECG signal from each sensing channel 83 and 85 may each be converted to a multi-bit digital signal by sensing module 86 and provided to cardiac signal analyzer 90. As described below, upon each ventricular sense event signal, cardiac signal analyzer 90 samples signal sample points from the respective ECG signals before and after the sensing threshold crossing for use in analyzing the ECG signal for TWOS detection.

Tachyarrhythmia detector 94 performs detection algorithms for discriminating shockable and non-shockable rhythms. Tachyarrhythmia detector 94 may analyze one or both ECG signals received from sensing channels 83 and 85 to determine if shockable rhythm detection criteria are met. If shockable rhythm detection criteria are met, control module 80 controls therapy delivery module 84 to deliver a shock therapy according to programmed therapy control parameters.

Cardiac signal analyzer 90 may further include a timing circuit 92 that includes various timers and/or counters for determining time intervals between sensed events, e.g., RR intervals, RT intervals, TR intervals, or other sensed cardiac event intervals used by tachyarrhythmia detector 94 for detecting TWOS and for detecting shockable rhythms. Tachyarrhythmia detector 94 may count RR intervals measured by timing circuit 92 that fall into different rate detection zones for determining a ventricular rate or performing other rate- or interval-based assessment for detecting a shockable rhythm. Timing circuit 92 may be configured to set various device controlled time intervals, e.g., pacing escape intervals, ECG signal analysis time segments or other time intervals used by cardiac signal analyzer 90 for monitoring the patient's heart rhythm and for controlling delivered therapies.

Examples of algorithms that may be performed by cardiac signal analyzer 90 for detecting shockable rhythms, which may be adapted to include techniques described herein using are generally disclosed in U.S. Pat. No. 8,160,684 (Ghanem, et al.) and U.S. Pat. No. 8,437,842 (Zhang, et al.), both of which patents are incorporated herein by reference in their entirety. The detection algorithms are highly sensitive and specific for the presence or absence of life threatening, shockable VT and VF.

Therapy delivery module 84 includes a high voltage (HV) therapy delivery module including one or more HV output capacitors. When a shockable rhythm is detected, the HV capacitors are charged to a pre-programmed voltage level by a HV charging circuit. Control module 80 applies a signal to trigger discharge of the HV capacitors upon detecting a feedback signal from therapy delivery module 84 that the HV capacitors have reached the voltage required to deliver a programmed shock energy. In this way, control module 80 controls operation of the high voltage output circuit of therapy delivery module 84 to deliver high energy CV/DF shocks using defibrillation electrode 24 and housing 15.

It is noted that implemented shockable rhythm detection algorithms may utilize not only ECG signal analysis methods but may also utilize supplemental sensors 96, such as blood pressure, tissue oxygenation, respiration, patient activity, patient posture, heart sounds, and the like, for contributing to a decision by control module 80 to apply or withhold a therapy.

Programmable control parameters may be programmed into memory 82 via telemetry module 88. Telemetry module 88 includes a transceiver and antenna for communicating with external device 40 (shown in FIG. 1) using RF communication as described above. Under the control of control module 80, telemetry module 88 may receive downlink telemetry from and send uplink telemetry to external device 40.

Figure 4:
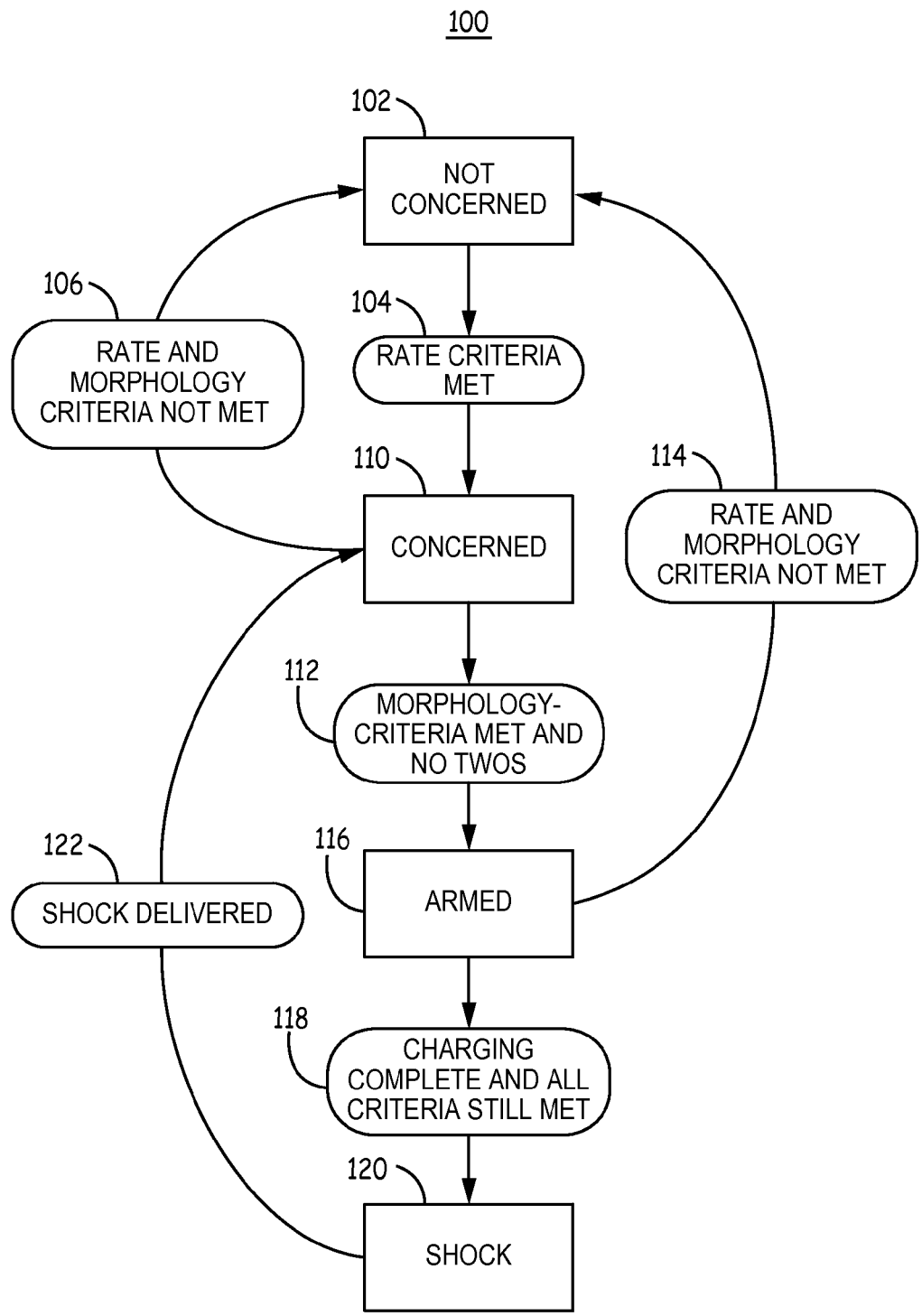
FIG. 4 is a state diagram providing an overview of a shockable rhythm detection scheme performed by the ICD of FIG. 1 according to one example.

FIG. 4 is a state diagram 100 providing an overview of a shockable rhythm detection scheme performed by ICD 14 according to one example. In some examples, ICD 14 operates in one of four states, Not Concerned state 102, Concerned state 110, Armed state 116 and Shock state 120. In the Not Concerned state 102, cardiac signal analyzer 90 determines RR intervals from ventricular sense event signals from one or both of ECG1 and ECG2 received from sensing channels 83 and 85.

In the illustrative examples described herein, both ECG1 and ECG2 are analyzed simultaneously for shockable rhythm detection. It is recognized that only one of ECG1 and ECG2 may be analyzed in other examples or if more than two sensing channels 83 and 85 are available, more than two ECG signals may be evaluated. In some cases, one of ECG1 and ECG2 may be analyzed for some portions of the analyses performed in states 102, 110, 116 and 120 and the other of ECG1 and ECG2 and/or both ECG1 and ECG2 may be analyzed for other portions of the analyses performed in states 102, 110, 116 and 120. For example, both ECG1 and ECG2 may be analyzed unless it is determined that one is corrupted by noise, in which case the noisy channel may be ignored and only the channel not corrupted by noise is used.

The RR intervals are used to determine if rate detection criteria are met. In some examples, analysis and detection of TWOS is not performed during the Not Concerned state 102. As a result the ventricular sense event signals used to determine RR intervals and determine if rate detection criteria are met may include oversensed T-waves. During the Not Concerned state 102, however, analysis to identify oversensed T-waves may not be performed and therefore correction of determined RR intervals is not performed.

The RR intervals may be compared to interval thresholds to determine if rate detection criteria are met. A heart rate estimate may be determined from RR intervals and is compared to rate detection criteria during the Not Concerned state 102. The heart rate may be estimated and compared to rate detection criteria on a beat-by-beat basis. If rate criteria are met (block 104), based on intervals determined between ventricular sensed event signals, the ICD 14 transitions to the Concerned state 110.

In one example, the RR interval ending with each sensed event is determined and stored in a buffer to accumulate a predetermined number of the most recent RR intervals, e.g., twelve RR intervals. Two separate buffers may be updated beat-by-beat for each of the two ECG sensing channels 83 and 85. To estimate the current heart rate for a given sensing channel 83 or 85, the associated buffer is sorted from shortest to longest RR intervals. The heart rate estimate may be determined as the nth shortest RR interval stored in the buffer. In one example, the heart rate estimate is the ninth shortest RR interval (i.e., only three of the twelve RR intervals currently stored in the buffer are longer than the selected RR interval heart rate estimate). Because oversensing is more common than undersensing when R-waves are sensed from an ECG signal that is acquired using extracardiac electrodes, a relatively longer one of the buffered RR intervals decreases the likelihood of overestimating the heart rate due to undersensing than a heart rate estimate based on an average, median, all of or a shorter one of the buffered RR intervals. Reasonable sensitivity to short R-R intervals in the case of VT or VF, however, is maintained.

If at least one of the estimated heart rate intervals of the two ECG channels is longer than a programmed rate detection threshold, ICD 14 remains in the Not Concerned state 102. The lower one of the two HR estimates is more likely to be the correct one, because oversensing is a more common occurrence than undersensing using extracardiac electrodes. If both heart rate estimate intervals are shorter than the programmed rate detection threshold, the ICD 14 advances to the Concerned state 110. A programmed rate detection threshold may be an interval of 333 ms corresponding to heart rate of 180 beats per minute (bpm). In other examples, other determinations of an estimated heart rate based on RR intervals determined between ventricular sense event signals and rate-based detection criteria may be used during the Not Concerned state 102. The methods disclosed herein are not limited to particular rate-based analysis and detection criteria that cause ICD 14 to transition from the Not Concerned state 102 to the Concerned state 110.

In the Concerned state 110, morphological analysis of the ECG signals from sensing channels 83 and 85 is performed to confirm the rate-based detection of a concerning rhythm in the Not Concerned state 102. The morphology criteria analyzed during the Concerned state may include ECG signal morphology analysis, such as gross morphology and/or beat-based morphology, that confirms that the morphology of the ECG signal in addition to the rate of the sensed events both meet shockable rhythm detection criteria before delivering a shock therapy. If the morphology criteria are not met and the rate detection criteria are no longer met (block 106) during the Concerned state 110, ICD 14 returns to the Not Concerned state 102.

In addition, detection of TWOS during the Concerned State 110, even if rate detection criteria and morphology detection criteria are met, prevents detection of a shockable rhythm. If TWOS is detected, the ICD 14 will remain in the Concerned state 110 as along as the rate detection criteria continues to be met; ICD 14 will not advance to the Armed state 116 if TWOS is detected.

If the morphology criteria are met, and no TWOS is detected (block 112), the ICD 14 advances to the Armed state 116. During the Armed state 116, cardiac signal analyzer 90 continues to perform the rate analysis performed during the Not Concerned state 102 and the morphology analysis and TWOS detection analysis performed during the Concerned state 110 while control module 80 begins charging the HV capacitors of therapy delivery module 84. If the shockable rhythm self-terminates during capacitor charging, such that rate and morphology criteria are no longer met (block 114) upon completion of capacitor charging, ICD 14 transitions from the Armed state 116 to the Not Concerned state 102. In another example, if shockable rhythm detection criteria are no longer met during the Armed state 116 due to TWOS detection as described in greater detail below, ICD 14 transitions back to the Not Concerned state 102.

If charging is complete and all detection criteria are still being met, including rate criteria, morphology criteria, and no TWOS, ICD 14 transitions to the Shock state 120 and delivers a CV/DF shock. As described in detail below, all detection criteria required to be met before advancing to the Shock state 120 may include rate criteria and a required number of n-second segments being classified as shockable after determining that TWOS detection criteria are not met.

After the shock is delivered (block 122), ICD 14 automatically transitions back to the Concerned state 110 to quickly redetect the shockable rhythm if the CV/DF shock was unsuccessful in restoring a normal heart rhythm.

Figure 5:
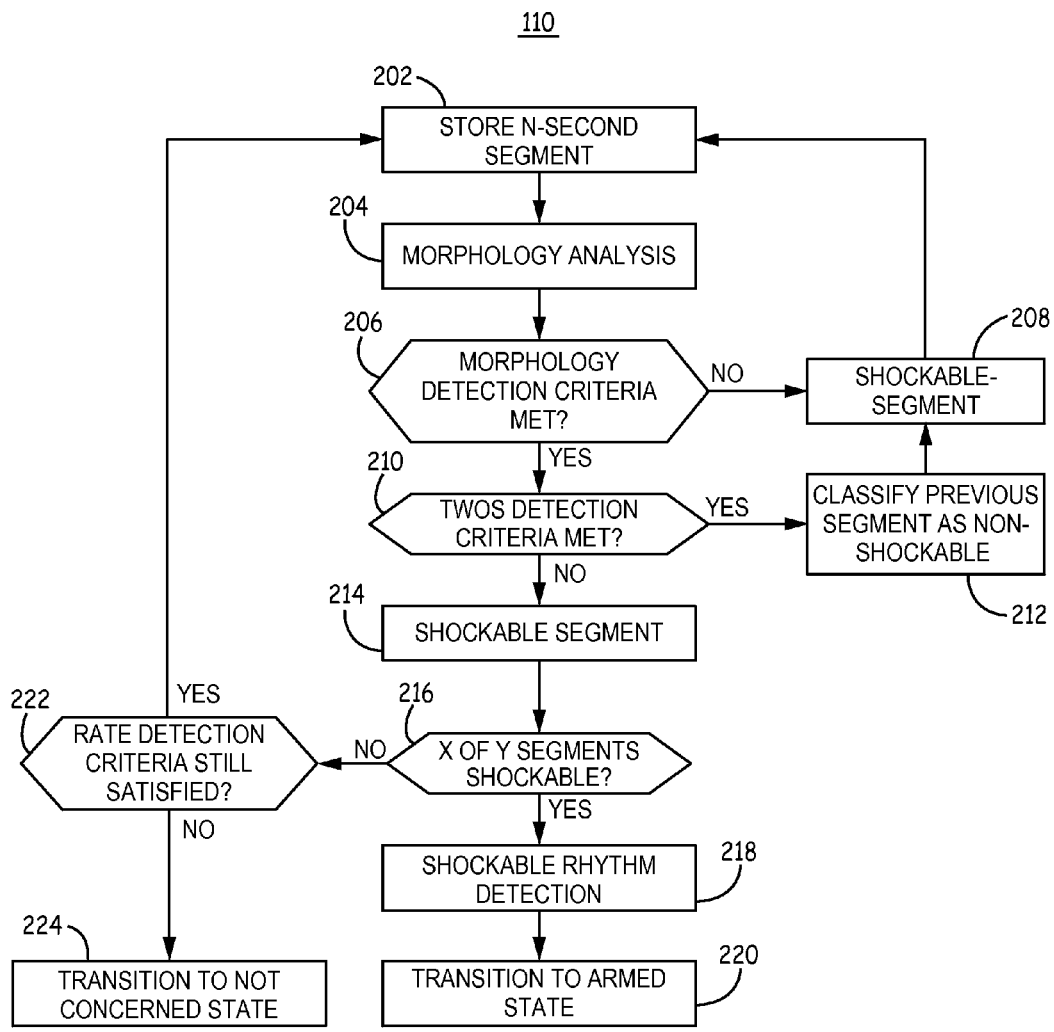
FIG. 5 is a flow chart of operations performed by the ICD of FIG. 1 during a Concerned state.

FIG. 5 is a flow chart of operations performed by ICD 14 during the Concerned state 110. During the Concerned state 110, morphology analysis may be performed over n-second ECG signal segments, and each n-second segment is classified as shockable or non-shockable. In one example, the morphology analysis is performed on 3-second ECG signal segments. If at least x out of y consecutive segments are classified as shockable, e.g., if two out three consecutive n-second segments are classified as shockable, in some or all ECG sensing channel signals being analyzed, e.g., one or both of the ECG signals from sensing channels 83 and 85, and TWOS detection criteria are not met, a shockable rhythm detection is made. ICD 14 transitions from the Concerned state 110 to the Armed state 116. This process is now described in more detail in conjunction with FIG. 5.

At block 202, a digitized n-second segment of the ECG signal is stored in a memory buffer. The n-second segment need not be timed relative to a sensed cardiac event and may therefore include a variable number of sensed cardiac events. Morphology analysis is performed at block 204 to determine if the ECG morphology during the n-second segment corresponds to a shockable rhythm ECG morphology. Morphology analysis may include signal noise analysis, gross morphology analysis, and beat-based morphology analysis.

Noise analysis may include determining a noise to signal ratio, a mean period, muscle noise pulse count, or other noise metrics. Examples of methods for detecting noise corruption of the n-second segment are generally disclosed in the above-incorporated '843 patent (Zhang, et al.) and in commonly-assigned U.S. Pat. No. 7,734,333 (Ghanem, et al.), incorporated herein by reference in its entirety.

Gross morphology analysis may include a determination of the low slope content (LSC), mean rectified amplitude, spectral width, or other metrics that discriminate between the ECG gross morphology of a shockable rhythm and a non-shockable rhythm. Beat-based morphology analysis may include a determination of a matching score or correlation of unknown beat signals to known beat signals using normalized waveform area difference (NWAD) or other template-based waveform morphology metrics of individual sensed ventricular event signals within the n-second segment. The techniques disclosed herein for rejecting a morphology based shockable segment classification based on TWOS detection are not limited to a particular ECG morphology analysis performed at block 204. Any of the examples above or other ECG signal morphology analyses may be performed, such as a wavelet transformation and template matching analysis, determining individual beat features such as slopes, areas, widths, signal peaks, signal polarities, and so on.

If morphology detection criteria are not met at block 206 for the current n-second segment, the segment is classified as non-shockable at block 208. TWOS detection criteria do not need to be applied to the n-second segment before finalizing the segment classification as non-shockable. The cardiac signal analyzer returns to block 202 to analyze the next n-second segment. If the morphology analysis of the n-second segment yields a shockable segment classification, however, based on noise analysis, gross ECG signal morphology analysis and/or beat-based sensed event morphology analysis, as determined at block 206, TWOS detection criteria are applied to the n-second segment at block 210, before classifying the segment. Examples of TWOS detection criteria are described in greater detail in conjunction with the flow chart 300 of FIG. 6.

If TWOS detection criteria are met at block 210, the previous n-second segment, i.e., the n-second segment preceding the current n-second segment being analyzed, is classified as non-shockable at block 212. If the preceding n-second segment was previously classified as shockable, it is reclassified as non-shockable at block 212 in response to the TWOS detection criteria being met during the current n-second segment. If the preceding n-second segment was previously classified as non-shockable, the non-shockable classification is maintained. The current n-second segment is also classified as non-shockable at block 208 in response to the TWOS detection criteria being met at block 210. The cardiac signal analyzer 90 moves to the next n-second segment for analysis as long as the rate detection criteria remain satisfied, which is most likely the case due to TWOS. No rate correction based on TWOS detection needs to be performed for re-determining a heat rate estimate. The final classification of the n-second segment is based on TWOS detection (or no TWOS detection) without re-determining a corrected heart rate estimate by excluding T-waves to verify whether or not rate-based criteria are still met.

If TWOS detection criteria are not met at block 210 for the current n-second segment, the segment is classified as shockable at block 214. At block 216, tachyarrhythmia detector 94 determines if shockable rhythm detection criteria are met at block 216, e.g., based on a requisite number of n-second segments being classified as shockable. For instance, if x out of the most recent y n-second segments, e.g., two out of three of the most recent 3-second segments are classified as shockable, a shockable rhythm detection is made at block 218 for the ECG sensing channel 83 or 85 that the n-second segments were obtained from. In some examples, a requisite number of n-second segments must be classified as shockable for both of the two ECG signals received from sensing channels 83 and 85. In other examples, a requisite number of n-second segments must be classified as shockable for only one of the two ECG signals received from sensing channels 83 and 85 to determine that the shockable rhythm detection criteria are met. In still other examples, only a single sensing channel is analyzed. In response to shockable rhythm detection criteria being met, the ICD 14 transitions to the Armed state at block 220 to begin capacitor charging for CV/DF shock delivery.

In some examples, both channels 83 and 85 must reach the required number of shockable segment classifications in order for a shockable rhythm detection to be made and to advance to the Armed state 116 at block 220. When both channels 83 and 85 are used, if TWOS detection criteria are met for one sensing channel 83 or 85 at the expiration of a single n-second segment out of the most recent y segments, this TWOS detection prevents a shockable rhythm detection from being made.

If the requisite number of shockable segments has not been reached at block 216, a shockable rhythm detection is not made. As long as the rate detection criteria are still satisfied (block 222), e.g., based on a heart rate estimate as described above in conjunction with FIG. 4, the ICD 14 remains in the Concerned state 110. Cardiac signal analyzer 90 analyzes the next n-second segment at block 202. As described above in conjunction with state diagram 100 of FIG. 4, if the rate detection criteria are no longer met as determined at block 222 during the Concerned state 110, the ICD 14 transitions back to the Not Concerned state at block 224.

Figure 6:
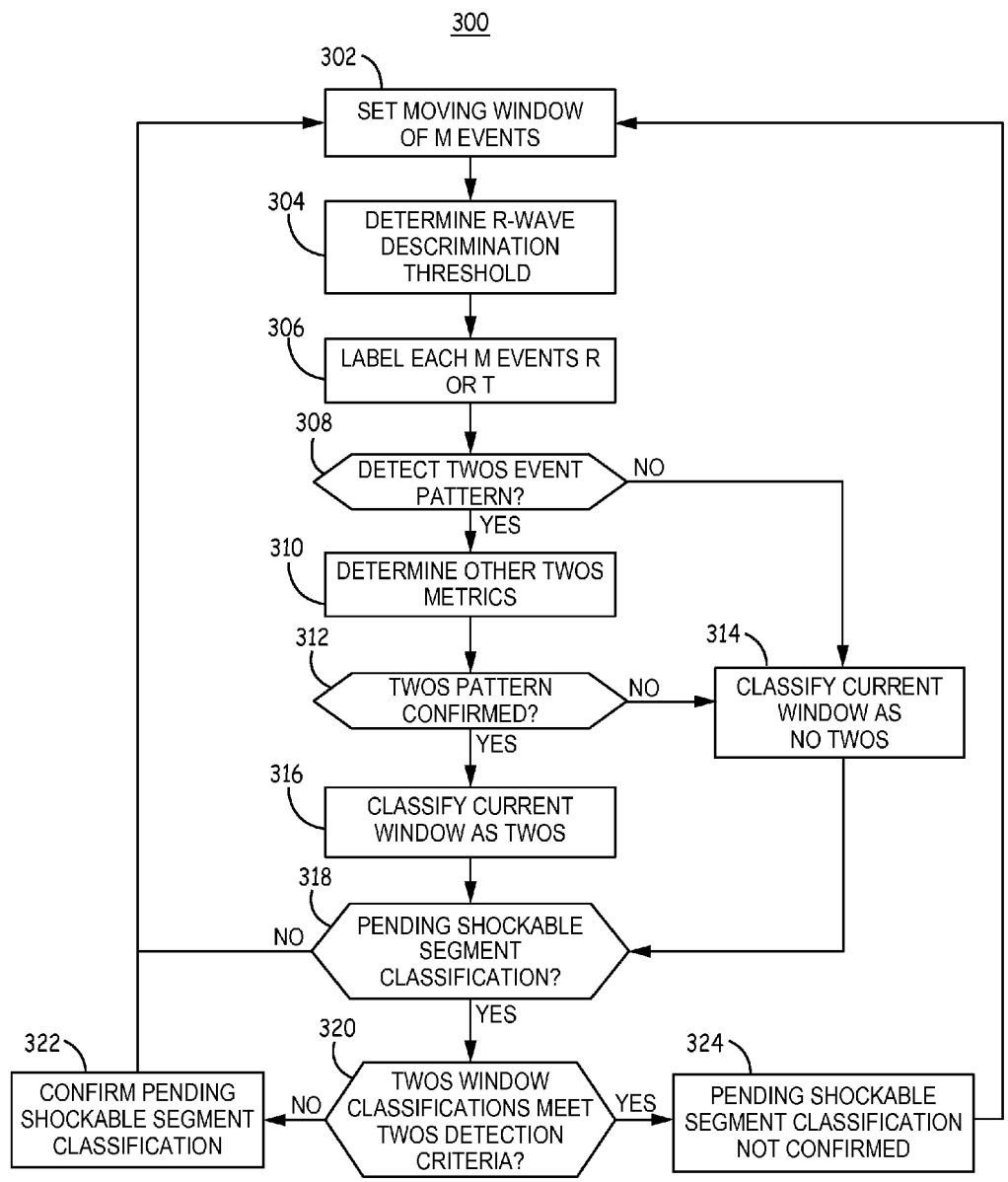
FIG. 6 is a flow chart of a method for determining if TWOS detection criteria are met.

FIG. 6 is a flow chart 300 of a method for determining if TWOS detection criteria are met at block 210 of FIG. 5. The cardiac signal analyzer 90 may be performing the method shown by flow chart 300 in the background during the Not Concerned state 102 and during the Concerned state 110 such that when a segment is classified as a shockable segment based on morphology detection criteria being met, TWOS classifications of successive groups of m sensed events are available for applying TWOS detection criteria at block 210 of FIG. 5. FIGS. 5 and 6 are described in the context of Concerned state 110. It should be recognized that the processes described herein for detecting TWOS for rejecting a pending shockable classification of an n-second ECG signal segment may also be performed in the Armed state 116 for classifying n-second signal segments and verifying that shockable rhythm detection criteria are still satisfied upon completion of capacitor charging.

Now referring to FIG. 6, at block 302 a moving window of m sensed events is advanced by one event upon each new sensed event. The oldest sensed event is discarded. As will be described, groups of m sensed events are analyzed for TWOS so that upon each sensed event, a preceding group of m sensed events is classified as TWOS or no TWOS. The beat-by-beat TWOS classifications of m-sensed event windows are used at block 210 of FIG. 5 to determine if TWOS detection criteria are met during the Concerned state 110. In one example, the moving window includes the current sensed event and the most recent five preceding events for a total of six most recently sensed events. For a given window of m-sensed events, an R-wave discrimination threshold is determined at block 304 from the m sensed events.

Figure 7:
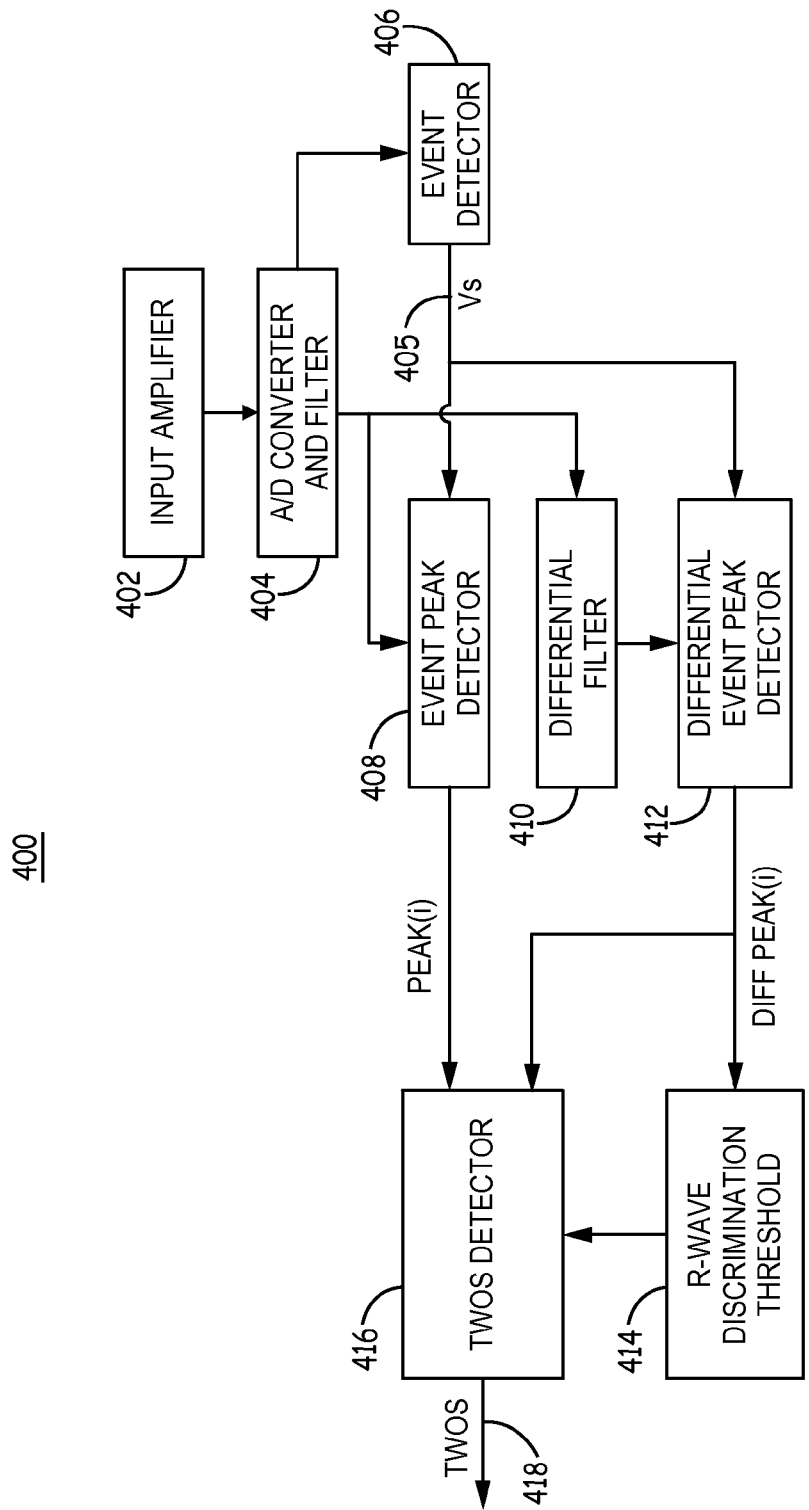
FIG. 7 is a schematic diagram of components that may be included in an electrical sensing module and a cardiac signal analyzer of the ICD of FIG. 1.

FIG. 7 is a schematic diagram 400 of components that may be included in electrical sensing module 86 and cardiac signal analyzer 90 for determining an R-wave discrimination threshold at block 304 of FIG. 6 and for classifying an m-sensed event window as TWOS according to one example. The apparatus and techniques represented by diagram 400 pertain to each ECG sensing channel 83 and 85. Each ECG signal channel 83 and 85 of electrical sensing module 86 may include an input amplifier 402 for receiving the ECG signal developed across the respective electrodes coupled to the sensing channel, an ND converter and filter 404 and an event detector 406.

The amplified ECG signal from input amplifier 402 is converted to a digital signal by A/D converter and filter 404 and digitally filtered by a bandpass filter, e.g., a pass band of 10 to 32 Hz. The filtered digital signal is provided to cardiac event detector 406 that uses an auto-adjusting R-wave sensing threshold set based on the peak amplitude of the currently sensed event. Upon a threshold crossing, a ventricular event is sensed and the peak of the sensed event is tracked and used to set the starting point of the R-wave sensing threshold for sensing the next ventricular event (after a refractory period). When the auto-adjusted R-wave sensing threshold is crossed a V sense (Vs) event signal 405 is passed from electrical sensing module 86 to cardiac signal analyzer 90.

Cardiac signal analyzer 90 receives Vs event signal Vs 405 and the filtered digital signal from A/D converter and filter 404. Cardiac signal analyzer 90 includes an event peak detector 408, a differential filter 410 and a differential signal event peak detector 412. The event peak detector 408 samples the filtered digital signal before and after each Vs event signal. In one example, the filtered digital signal is sampled at 256 Hz for 4 samples prior to the Vs event signal and 24 samples after the Vs event signal by event peak detector 408. The maximum signal amplitude of the samples is identified as the peak amplitude of the sensed event. The peak amplitude of each ith event (PEAK(i)) in the m-sensed event window is provided as input to TWOS detector 416.

The filtered digital signal from ND converter and filter 404 is also provided to a differential filter 410. Differential filter 410 determines a first order differential signal, e.g., as given by $Y(i)=x(i)-x(i-1)$ where $x(i)$ is the current sample point amplitude and $x(i-1)$ is the preceding signal sample point amplitude. In other examples another form of high pass or band pass filter may be used to obtain a high pass filtered signal of the original filtered digital signal. R-waves are expected to have a higher frequency band than T-waves in a given ECG signal. The high pass filtering effect of the differential filter 410 should attenuate T-wave amplitudes more than R-wave amplitudes, increasing the amplitude difference between Vs events that are R-waves and Vs events that are oversensed T-waves.

The differential filtered signal is passed to a differential event peak detector 412, which samples the differential filtered signal before and after the Vs event signal 405 and determines the differential signal peak amplitude, DIFF PEAK(i), of each sensed event during the m-sensed event window. The differential filtered signal may be sampled at 256 Hz to obtain four sample points before the Vs event signal 405 and 24 sample points after the Vs event signal 405 in one example. The differential peak amplitude DIFF PEAK(i) of each Vs event during the m-sensed event window is provided as input to processing block 414. Processing block 414 computes the R-wave discrimination threshold for the current m-sensed event window using the m differential event peak amplitudes, e.g., DIFF PEAK(1) through DIFF PEAK(6) of a window including six Vs event signals. The event peak amplitudes, DIFF PEAK (i), of the differential signal are also provided as input to the TWOS detector 416.

R-wave discrimination threshold processing block 414 determines the R-wave discrimination threshold that separates the more highly attenuated T-waves of the differential filtered signal from the less attenuated R-waves. In one example, the R-wave discrimination threshold is computed by determining a maximum peak from groups of three consecutive DIFF PEAK(i) values in the m-sensed event window. If the m-sensed event window includes six Vs events, the maximum of DIFF PEAK(1), DIFF PEAK(2) and DIFF PEAK(3) is determined as MAX(1). The maximum of DIFF PEAK(4), DIFF PEAK(5) and DIFF PEAK (6) is determined as MAX(2). These two maximum peak amplitudes MAX(1) AND MAX(2) are averaged to determine the R-wave discrimination threshold. The R-wave discrimination threshold may be set as a predetermined percentage of the averaged maximum. In one example, 43.75% of the averaged maximum peak amplitude is set as the R-wave discrimination threshold.

Processing block 414 determines maximum peak amplitudes from the DIFF PEAK(i) values selected three at a time because noise signals may be more common on ECG signals obtained from extracardiac electrodes than in cardiac electrical signals obtained from intracardiac or epicardial electrodes. As such, out of every three Vs event signals, one event may be a true R-wave, one event may be TWOS and one event may be noise. By determining one maximum peak from DIFF PEAK(i) values selected three at time (consecutively), the maximum one of the three is expected to be a true R-wave. If taken two at a time, a maximum peak out of a noise signal and a T-wave may be identified which would confound the discrimination between R-waves and T-waves.

The R-wave discrimination threshold is provided as input to TWOS detector 416 for comparison to each DIFF PEAK (i). If a given DIFF PEAK(i) crosses the R-wave discrimination threshold, i.e., is greater than or equal to the R-wave discrimination threshold, the PEAK(i) and DIFF PEAK(i) received for that Vs event are labeled as R-waves. If the DIFF PEAK(i) does not cross the R-wave discrimination threshold, i.e., is less than the R-wave discrimination threshold, the PEAK(i) and DIFF PEAK(i) received for that Vs event are labeled as T-waves. In this way, TWOS detector 416 has m peak amplitudes from the filtered digital signal and m peak amplitudes from the differential filtered signal for the m-sensed event window with each peak labeled "R" or "T". TWOS detector 416 is configured to analyze these "R" and "T" labeled peaks for detecting TWOS and classifying the m-sensed event window as TWOS or no TWOS.

Referring again to FIG. 6, after determining the R-wave discrimination amplitude at block 304, each of the m sensed events in the current window are labeled "R" for R-wave or "T" for T-wave based on the R-wave discrimination threshold as described above. The now labeled m sensed events are evaluated at block 308 by TWOS detector 416 to determine if a TWOS event pattern exists. To detect a TWOS pattern, an event labeled T must follow an event labeled R, i.e., R-T. In some examples, at least two of these R-T pairs must be identified during the m-sensed event window to detect a TWOS event pattern at block 308. The two R-T pairs need not be consecutive but must be mutually distinct R-T pairs. If a TWOS event pattern is not detected, the cardiac signal analyzer 90 classifies the current m-sensed event window as No TWOS at block 314.

If at least two R-T pairs are identified, other TWOS metrics may be determined at block 310 to verify the detected R-T pattern of sensed events. In order to verify that the at least two R-T pairs are valid R-wave and T-wave events, metrics of R-wave amplitude stability, T-wave amplitude stability, R-T interval stability and/or the frequency difference between the R-wave and the T-wave may be determined at block 310. Example methods for verifying R-T pairs are generally disclosed in U.S. Pat. No. 7,831,304 (Cao), incorporated herein by reference in its entirety. Each of these other metrics determined to verify valid R-T pairs may be determined using only R-labeled events and T-labeled events that constitute the identified R-T pairs within the m-sensed event window. Other events, R or T, that do not follow the required R-T pattern may be excluded from this analysis. For example, if six events are identified as R-R-T-T-R-T, the oldest event labeled R and the fourth event labeled T may be excluded from the analysis performed at block 310 to determine other TWOS metrics. The second and third events are identified as one R-T pair and the fifth and sixth event are identified as another R-T pair. These four events are used to determine other TWOS metrics used to verify that these two pairs are valid R-T pairs.

For example, with reference to FIG. 7, to verify R-wave amplitude stability each PEAK(i) labeled "R" and identified in an R-T pair from event peak detector 408 and/or each DIFF PEAK(i) labeled "R" and identified in an R-T pair from differential event peak detector 412 may be verified to be within an acceptable range of each of the other respective R-labeled peaks included in R-T pairs in the m-sensed event window. In one example, to verify R-wave peak amplitude stability, the DIFF PEAK (i) values that are labeled "R" and included in an R-T pair are averaged to determine an average differential R-wave peak amplitude. The difference between each DIFF PEAK (i) labeled "R" and the average differential R-wave peak amplitude is determined and compared to a threshold. The threshold may be a percentage, e.g., 50%, of the average differential R-wave peak amplitude. If each difference between the DIFF PEAK(i) values labeled "R" in identified R-T pairs and the average differential R-wave peak amplitude is less than the threshold, the corresponding R-labeled events are deemed a valid R-wave based on amplitude stability.

The T-wave amplitude stability may be verified in a similar manner using the PEAK(i) values and/or the DIF PEAK(i) values labeled "T" and identified in R-T pairs. In one example, PEAK(i) values and/or DIFF PEAK(i) values for each T-labeled event of each R-T pair may be analyzed to verify that the T-wave amplitudes of the filtered digital signal and/or the attenuated T-wave amplitudes of the differential filtered signal are stable. To illustrate, an average of the PEAK(i) values (AVG PEAK(i)) and an average of the DIFF PEAK(i) values (AVG DIFF PEAK(i)) for each T-labeled event of the R-T pairs are determined. The difference between each DIFF PEAK(i) and the AVG DIFF PEAK(i) is compared to a maximum threshold, which may be a percentage of the AVG DIFF PEAK(i), e.g., 50%. A difference less than the threshold is evidence that the DIFF PEAK(i) is associated with a valid T-wave. Additionally, the difference between each PEAK(i) and the AVG PEAK(i) is compared to a maximum threshold, e.g., 50% of the AVG PEAK(i). If both of these differences, DIFF PEAK(i)–AVG DIFF PEAK (i) and PEAK(i)–AVG PEAK(i), for a given T-labeled event are less than their respective maximum thresholds, the T-labeled event is deemed a valid T-wave based on amplitude stability.

Another metric that may be determined at block 310 by TWOS detector 416 is a metric of the difference in R-wave signal frequency and T-wave signal frequency in the identified R-T pairs. This frequency difference is represented by the greater attenuation of the T-wave in the differential filtered signal than the R-wave signal and may therefore be evaluated based on an analysis of the relative changes in peak amplitudes between the filtered digital signal and the differential filter signal.

In one example, the product of AVG DIFF PEAK(i) determined from the T-labeled events of identified R-T pairs and the AVG PEAK(i) determined from R-labeled events of the identified R-T pairs is compared to a threshold. When the T-labeled events are valid T-waves, this first product should decrease due to greater attenuation of valid T-waves in the differential signal compared to when the T-labeled events are low amplitude R-waves (which may occur during a shockable rhythm). The threshold may be defined as a percentage (e.g., 62.5% or in the range of 50% to 70%) of the product of the AVG DIFF PEAK(i) of R-labeled events and AVG PEAK(i) of T-labeled events of the identified R-T pairs. This second product should not decrease substantially when the R-labeled events are valid R-waves because the higher frequency R-waves are less attenuated in the differential peak signal. If the first product is less than a predetermined percentage of the second product, indicating substantial attenuation of valid T-waves and insubstantial attenuation of valid R-waves in the differential filtered signal, R-T pairs have met an R-T frequency discrimination criterion for validating the identified R-T pairs.

Other TWOS metrics that may be determined at block 310 may include a metric of R-T interval stability of the identified R-T pairs. TWOS detector 416 may determine the time interval between the R-labeled event and the T-labeled event of each R-T pair identified during the m-sensed event window. An average R-T interval may be determined from the R-T time intervals. If each R-T interval is within an acceptable range of the R-T interval average, e.g., within 50% of the average, the R-T intervals are deemed stable and have met an R-T interval stability criterion for confirming the identified R-T pairs.

If R-wave amplitude stability criteria, T-wave amplitude stability criteria, R-T frequency difference criteria and/or R-T interval stability criteria are met, as determined at block 312, the identified TWOS pattern detected at block 308 is confirmed. The current m-second window is classified as TWOS at block 316 by the TWOS detector 416. A TWOS detect signal 418 (FIG. 7) is provided to tachyarrhythmia detector 94 (FIG. 3) for use in confirming a pending shockable segment classification if needed, as determined at decision block 318. If the identified R-T pairs are not confirmed based on R-wave amplitude stability, T-wave amplitude stability, R-T frequency difference, and/or R-T interval stability, the current m-sensed event window is classified as no TWOS at block 314.

The operations described in conjunction with blocks 302 through 316 may be performed in the Not Concerned state 102 (FIG. 4) and in the Concerned state 110 such that if ICD 14 transitions to the Concerned state and morphology detection criteria become satisfied, the TWOS detect signals 418 generated after each Vs event ending consecutive, overlapping m-sensed events windows are available for determining if TWOS is occurring during the n-second segment. If ICD 14 is not in the Concerned state 110 or in the Concerned state 110 but morphology detection criteria have not yet been satisfied (i.e., no pending shockable segment classification), as determined at decision block 318, the process shown by FIG. 6 returns to block 302 to advance to the next m-sensed event window.

If ICD 14 is in the Concerned state 110 and morphology detection criteria have been satisfied ("yes" branch of block 318), the tachyarrhythmia detector 94 analyzes the TWOS signals 418 received from TWOS detector 416 to determine if TWOS detection criteria are satisfied at block 320. In one example the TWOS signals 418 received from TWOS detector 416 for the preceding 18 Vs events, in other words for the preceding 18 m-sensed event windows, are evaluated to determine if TWOS detection criteria during the n-second segment are met. The TWOS detection criteria may include a required frequency or number of TWOS signals 418 out of the preceding 18 (or other number of) m-sensed event windows and a requirement of how recent or contemporaneous the latest of the TWOS signals 418 is with the morphology detection criteria being met at the end of the n-second segment.

To illustrate, if a TWOS signal 418 was received for at least three of the m-sensed event windows out of the most recent 18 consecutive overlapping windows and at least one of those TWOS signals was received within the most recent 9 of the consecutive overlapping windows, the TWOS detection criteria are met at block 320. It is recognized that numerous variations of the TWOS detection criteria used at block 320 may be established for detecting TWOS during the n-second segment based on the TWOS signals 418 received from T-wave detector 416. In other words, the TWOS classifications and the No TWOS classifications made at respective blocks 316 and 314 for a predetermined number of preceding m-sensed event windows may be used for determining if TWOS detection criteria are met at block 320.

If the TWOS detection criteria are not met ("no" branch of block 320), the pending shockable segment classification is confirmed at block 322. This confirmation corresponds to block 214 of FIG. 5. The tachyarrhythmia detector 94 may advance to block 216 of FIG. 5 to determine if shockable rhythm detection criteria are satisfied.

If the TWOS detection criteria are met, "yes" branch of block 320, the pending shockable segment classification based on morphology detection criteria is not confirmed at block 324. This corresponds to the "yes" branch of block 210 of FIG. 5. Both the preceding n-second segment and the current n-second segment are classified as non-shockable at blocks 212 and 208 as described previously.

After confirming or not confirming the pending shockable segment classification at respective blocks 322 and 324, monitoring for T-wave oversensing by T-wave detector 416 continues beat-by-beat by advancing the moving window at block 302 to the next Vs event and discarding the oldest Vs event.

Figure 8:
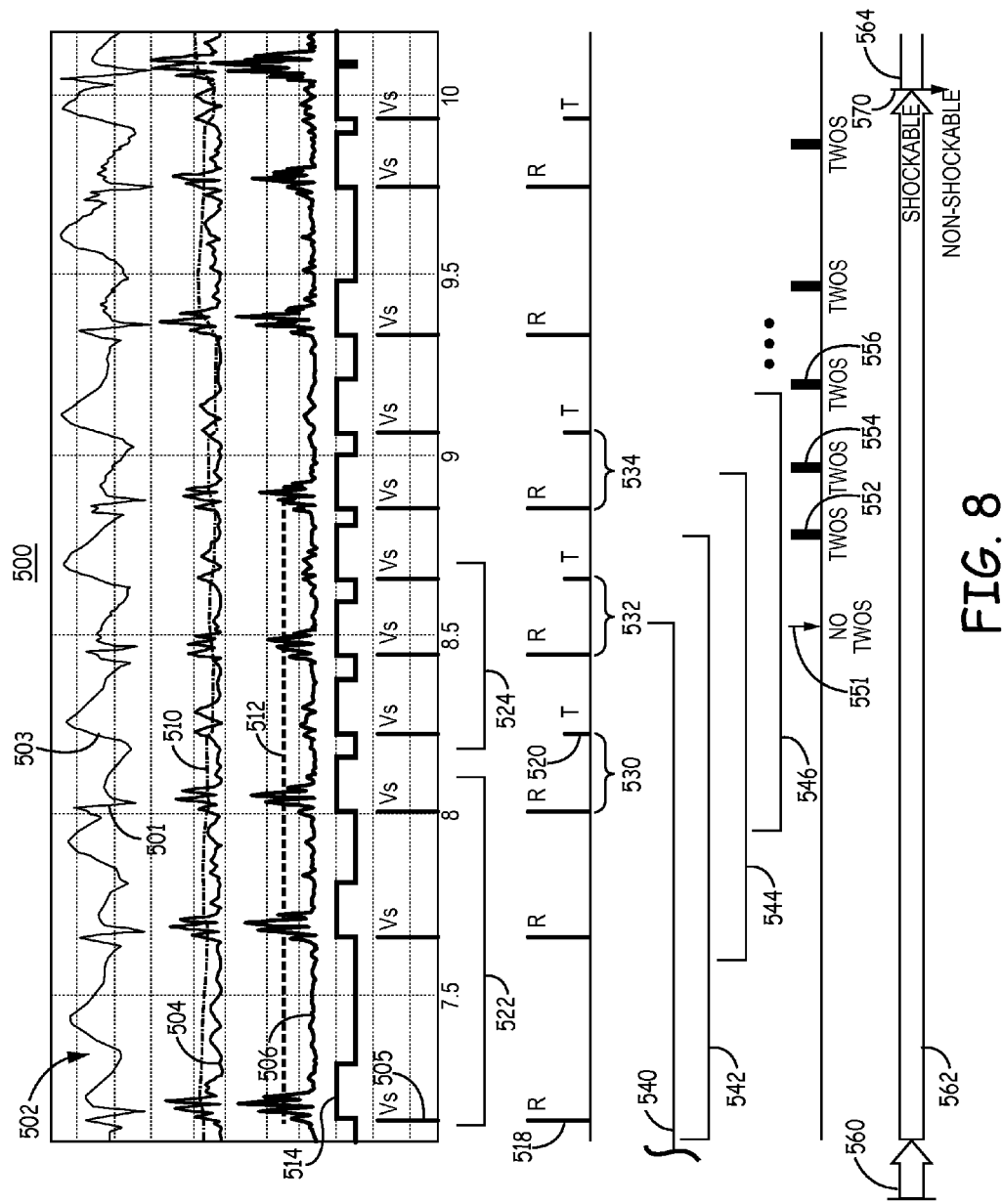
FIG. 8 is a depiction of an ECG signal and cardiac event sensing and TWOS detection as performed by the ICD of FIG. 1 according to one example.

FIG. 8 is a depiction 500 of an ECG signal 502 and cardiac event sensing and TWOS detection as performed by ICD 14. With reference to the schematic diagram of FIG. 4, ECG signal 502 is received by input amplifier 402 via a pair of extracardiac electrodes coupled to ICD 14, e.g., any pair of electrodes 28 and 30 and housing 15. ECG signal 502 includes relatively high frequency R-waves 501 followed by relatively low frequency T-waves 503. The T-waves 503 have a relatively high amplitude and are susceptible to oversensing. Filtered signal 504 is a rectified, filtered digital signal produced by A/D converter and filter 404 of sensing module 86 and is passed to event detector 406, event peak detector 408 and to differential filter 410. Differential filtered signal 506 is provided to differential event peak detector 412. In comparing filtered signal 504 and differential filtered signal 506, T-waves are substantially attenuated in the differential filtered signal 506 compared to filtered signal 504. The relative attenuation of the higher frequency R-waves in differential filtered signal 506 is less than the attenuation of the T-waves in the differential signal 506.

Event sensing threshold 510 is an auto-adjusted, decaying sensing threshold generated by event detector 406 based on peak amplitudes of sensed events of filtered signal 504. Based on crossings of event sensing threshold 510 by filtered signal 504, event detector 406 generates Vs event signals 505. Upon each Vs event signal 505, electrical sensing module 86 may apply a blanking interval 514 to avoid oversensing of the same ventricular event, e.g., to avoid double-sensing of R-waves. Blanking interval 514 is at least 150 ms in some examples to avoid double sensing of the R-waves 501, which have a relatively wider signal width than R-waves included in cardiac electrogram signals obtained by intracardiac or epicardial electrodes.

Event peak detector 408 samples filtered signal 504 before and after each Vs event signal 505 (including sampling during blanking intervals 514) to detect the rectified peak amplitude (PEAK(i)) of filtered signal 504 for each Vs event 505. These peak amplitudes PEAK(i) are provided to TWOS detector 416.

Differential event peak detector 412 samples differential filtered signal 506 before and after each Vs event signal 505 (including sampling during blanking intervals 514) to obtain differential filtered signal peak amplitudes (DIFF PEAK(i)) for each Vs event 505. These differential filtered signal peak amplitudes DIFF PEAK(i) are also provided to TWOS detector 416 and to R-wave discrimination threshold processing block 414.

TWOS detector 416 and processing block 414 set overlapping, windows 540, 542, 544, and 546, each including a predetermined number of Vs event signals 505. Windows 540 through 546 are set for analyzing the PEAK(i) and DIFF PEAK(i) signals included in each window for determining if TWOS is occurring in each respective window. Processing block 414 determines an R-wave discrimination threshold for each m-sensed event window 540, 542, 544 and 546 by analyzing the DIFF PEAK(i) values for the m events included in each m-sensed event window. In this example, each window 540, 542, 544 and 546 includes six Vs event signals 505.

The R-wave discrimination threshold 512 determined for one window 542 is shown. R-wave discrimination threshold 512 is determined by determining the maximum DIFF PEAK(i) for Vs events taken three at a time within window 542. In other words, the maximum DIFF PEAK(i) is determined for the first group of three Vs events 522 and the maximum DIFF PEAK (i) is determined for the last group of three Vs events 524. R-wave discrimination threshold 512 is the average of two maximums.

Each Vs event 505 is identified as an R-event 518 if differential filtered signal 506 crosses the R-wave discrimination threshold 512 or as a T-event 520 if differential filtered signal 506 does not cross R-wave discrimination threshold 512. TWOS detector determines if at least two R-T pairs, e.g., R-T pairs 530, 532 and 534, exist in a given window 540, 542, 544, or 546. Window 540 includes only one R-T pair 530. TWOS detector 416 determines no TWOS 551 for window 540. This may be tracked by a signal indicating no TWOS or no signal being generated by TWOS detector 416 may indicate to tachyarrhythmia detector that TWOS is not determined to be present in window 540.

Two R-T pairs 530 and 532 are identified in windows 542 and 544. Three R-T pairs 530, 532 and 534 are identified in window 546. The R-T pairs 530, 532 and 534 may be confirmed by analyzing R-wave amplitude stability, T-wave amplitude stability, R-T interval stability, and/or R and T frequency difference as described above in conjunction with FIG. 6. TWOS signals 552, 554 and 556 are produced by TWOS detector 416 for each respective window 542, 544 and 546.

Three-second ECG signal analysis segments 560 and 562 are shown. Tachyarrhythmia detector 94 analyzes filtered signal 504 over each three-second segment when ICD 14 is in the Concerned state 110 for determining if morphology detection criteria are met. In the example shown, a shockable segment classification of signal analysis segment 562 is pending at the end of the three-second segment 562 based on the morphology analysis. Tachyarrhythmia detector 94 may count Vs event signals 505 and TWOS signals 552, 554 and 556 to determine if TWOS detection criteria are met for the signal analysis segment 562. For example, tachyarrhythmia detector 94 may determine if a required number of TWOS signals have been received out of a predetermined number of VS event signals 505 immediately preceding the expiration of signal analysis segment 562.

In the illustrative example given above, at least three TWOS signals 552, 554 and 556 must be received within the last 18 Vs event signals 505 and the latest TWOS signal 556 must have been received within the last 9 Vs event signals 505. Since these TWOS detection criteria are met for signal analysis segment 562, tachyarrhythmia detector 94 classifies segment 562 as non-shockable 570 prior to making a shockable rhythm detection based on segment 562 and thereby precluding a transition into the Armed state 116 (FIG. 4) at the expiration of signal analysis segment 562. It should be noted that in some cases, classification of one or more windows, e.g., window 540, that include Vs event signals preceding signal analysis segment 562 may contribute to the TWOS detection made at the expiration of segment 562. As such, T-events 520 occurring during segment 562 are not the only oversensed T-waves that may contribute to a classification of segment 562 as a non-shockable segment.

In some examples, the preceding signal analysis segment 560 is reclassified as a non-shockable segment (if previously classified as shockable) in response to the TWOS detection criteria being satisfied for signal analysis segment 562. By reclassifying segment 560 as non-shockable, ICD 14 is prevented from transitioning from the Concerned state 110 to the Armed state 116 after the next subsequent signal analysis segment 564, regardless of the classification of segment 564 as non-shockable or shockable when the shockable rhythm detection criteria requires at least two out of three consecutive signal analysis segments be classified as shockable. In this way, the likelihood of shock delivery due to TWOS is reduced.

Thus, a method and apparatus for detecting TWOS for use in reducing the likelihood of falsely detecting a shockable rhythm and delivering an unneeded therapy have been presented in the foregoing description with reference to specific embodiments. In other examples, various methods described herein may include steps performed in a different order or combination than the illustrative examples shown and described herein. It is appreciated that various modifications to the referenced embodiments may be made without departing from the scope of the disclosure and the following claims.

The invention claimed is:

1. A method performed by a medical device, comprising:
  receiving a cardiac electrical signal from a patient's heart via a plurality of extracardiac electrode electrically coupled to the medical device;
  sensing cardiac events from the cardiac electrical signal;
  during a first operating state of the medical device, determining an estimated rate of the sensed cardiac events;
  transitioning from the first operating state to a second operating state of the medical device when the estimated rate of cardiac events meets a shockable rate detection criterion;
  setting a first signal analysis segment of the cardiac electrical signal during the second operating state;
  analyzing the first signal analysis segment to determine if shockable rhythm classification criteria are met for the first signal analysis segment;
  setting a plurality of T-wave oversensing (TWOS) analysis windows;
  analyzing cardiac events of the cardiac electrical signal to classify each TWOS analysis window of the plurality of TWOS analysis windows as one of TWOS and no TWOS, each TWOS analysis window being classified as TWOS when cardiac events during the TWOS analysis window satisfy TWOS criteria and classified as no TWOS when the cardiac events during the TWOS analysis window do not satisfy TWOS criteria;
  determining that TWOS detection criteria are met for the first signal analysis segment when a predetermined number of the plurality of TWOS analysis windows are classified as TWOS;
  classifying the first signal analysis segment as non-shockable in response to determining that the TWOS detection criteria are met; and
  remaining in the second operating state without advancing to a third operating state of the medical device when the TWOS detection criteria are met for the first signal analysis segment.

2. The method of claim 1, further comprising determining whether the TWOS detection criteria are met for the first signal analysis segment only after the shockable rhythm classification criteria are met for the first signal analysis segment.

3. The method of claim 1, further comprising classifying a second signal analysis segment preceding the first signal analysis segment as non-shockable when the TWOS detection criteria are met for the first signal analysis segment.

4. The method of claim 3, further comprising:
  sensing cardiac events from the cardiac electrical signal;
  during a first operating state of the medical device, determining an estimated rate of the sensed cardiac events;
  transitioning from the first operating state to a second operating state of the medical device when the estimated rate of the sensed cardiac events meets a shockable rate detection criterion;
  setting the first signal analysis segment and the second signal analysis segment during the second operating state; and
  remaining in the second operating state for a third signal analysis segment after the first signal analysis segment without advancing to a third operating state of the medical device when the TWOS detection criteria are met for the first signal analysis segment.

5. The method of claim 4, wherein receiving the cardiac electrical signal comprises receiving the cardiac electrical signal from a first sensing channel coupled to the plurality of extracardiac electrodes, the method further comprising:
  receiving a second cardiac electrical signal from a second sensing channel coupled to the plurality of extracardiac electrodes;
  analyzing the second cardiac electrical signal for classifying each of a plurality of fourth cardiac signal segments as one of shockable and not shockable; and
  remaining in the second operating state for the third signal analysis segment when the TWOS detection criteria are met for the first signal analysis segment and the plurality of fourth cardiac signal segments are classified as shockable.

6. The method of claim 4, further comprising:
  detecting a shockable rhythm when at least the third signal analysis segment is determined to meet shockable rhythm classification criteria and the TWOS detection criteria are not met for the third signal analysis segment;
  advancing to the third operating state from the second operating state when the shockable rhythm is detected; and
  charging a capacitor for delivering a shock therapy during the third operating state.

7. The method of claim 1, wherein analyzing cardiac events of the cardiac electrical signal comprises:
  selecting at least one group of at least three consecutive cardiac events from the plurality of cardiac events that are within a given one of the plurality of TWOS analysis windows;
  determining a maximum event amplitude from the at least one group;
  determining an event discrimination threshold using the maximum event amplitude;
  identifying as R-waves all cardiac events of the plurality of cardiac events within the given one of the plurality of TWOS analysis windows that are equal to or greater than the event discrimination threshold;
  identifying as T-waves all events of the plurality of cardiac events within the given one of the plurality of TWOS analysis windows that is less than the event discrimination threshold; and
  identifying a pattern of TWOS when each one of at least a portion of the identified R-waves is consecutively followed by one of the identified T-waves in an R-T pair.

8. The method of claim 7, further comprising:
verifying that the R-T pair is a valid R-T pair by verifying at least one of an R-wave amplitude stability, a T-wave amplitude stability, an R-T interval stability and an R-T frequency difference; and
classifying the given signal analysis segment as TWOS when at least two valid R-T T pairs within the given signal analysis segment are verified.

9. The method of claim 1, wherein determining that the TWOS detection criteria are met for the first signal analysis segment comprises determining that the TWOS detection criteria are met when a first predetermined number of the plurality of TWOS analysis windows are classified as TWOS and a second predetermined number of the plurality of TWOS analysis windows that are classified as TWOS occur within a third predetermined number of the plurality of TWOS analysis windows preceding the shockable rhythm classification criteria being met.

10. An implantable medical device, comprising:
a sensing module configured to receive a cardiac electrical signal via a plurality of extracardiac electrodes coupled to the implantable medical device ; and
a control module coupled to the sensing module and configured to:
set a first signal analysis segment of the cardiac electrical signal;
analyze the first signal analysis segment to determine if shockable rhythm classification criteria are met for the first signal analysis segment
set a plurality of T-wave oversensing (TWOS) analysis windows;
analyze cardiac events of the cardiac electrical signal to classify each TWOS analysis window of the plurality of TWOS analysis windows as one of TWOS and no TWOS, each TWOS analysis window being classified as TWOS when cardiac events during the TWOS analysis window satisfy TWOS criteria and classified as no TWOS when the cardiac events during the TWOS analysis window do not satisfy TWOS criteria;
determine that TWOS detection criteria are met for the first signal analysis segment when a predetermined number of the plurality of TWOS analysis windows are classified as TWOS, wherein the control module is further configured to determine whether the TWOS detection criteria are met for the first signal analysis segment only after the shockable rhythm classification criteria are met for the first signal analysis segment; and
classify the first signal analysis segment as non-shockable in response to determining that the TWOS detection criteria are met.

11. An implantable medical device, comprising:
a sensing module configured to receive a cardiac electrical signal via a plurality of extracardiac electrodes coupled to the implantable medical device ; and
a control module coupled to the sensing module and configured to:
set a first signal analysis segment of the cardiac electrical signal;
analyze the first signal analysis segment to determine if shockable rhythm classification criteria are met for the first signal analysis segment;
set a plurality of T-wave oversensing (TWOS) analysis windows;
analyze cardiac events of the cardiac electrical signal to classify each TWOS analysis window of the plurality of TWOS analysis windows as one of TWOS and no TWOS, each TWOS analysis window being classified as TWOS when cardiac events during the TWOS analysis window satisfy TWOS criteria and classified as no TWOS when the cardiac events during the TWOS analysis window do not satisfy TWOS criteria;
determine that TWOS detection criteria are met for the first signal analysis segment when a predetermined number of the plurality of TWOS analysis windows are classified as TWOS; and
classify the first signal analysis segment as non-shockable in response to determining that the TWOS detection criteria are met, wherein:
the sensing module is configured to sense cardiac events from the cardiac electrical signal;
the control module is further configured to:
determine an estimated rate of the sensed cardiac events during a first operating state of the medical device;
transition from the first operating state to a second operating state of the medical device when the estimated rate of cardiac events meets a shockable rate detection criterion;
set the first signal analysis segment during the second operating state; and
remain in the second operating state without advancing to a third operating state of the medical device when the TWOS detection criteria are met for the first signal analysis segment.

12. An implantable medical device, comprising:
a sensing module configured to receive a cardiac electrical signal via a plurality of extracardiac electrodes coupled to the implantable medical device; and
a control module coupled to the sensing module and configured to:
set a first signal analysis segment of the cardiac electrical signal;
analyze the first signal analysis segment to determine if shockable rhythm classification criteria are met for the first signal analysis segment;
set a plurality of T-wave oversensing (TWOS) analysis windows;
analyze cardiac events of the cardiac electrical signal to classify each TWOS analysis window of the plurality of TWOS analysis windows as one of TWOS and no TWOS, each TWOS analysis window being classified as TWOS when cardiac events during the TWOS analysis window satisfy TWOS criteria and classified as no TWOS when the cardiac events during the TWOS analysis window do not satisfy TWOS criteria;
determine that TWOS detection criteria are met for the first signal analysis segment when a predetermined number of the plurality of TWOS analysis windows are classified as TWOS; and
classify the first signal analysis segment as non-shockable in response to determining that the TWOS detection criteria are met,
wherein the control module is further configured to classify a second signal analysis segment preceding the first signal analysis segment as non-shockable when the TWOS detection criteria are met for the first signal analysis segment.

13. The device of claim 12, wherein:
the sensing module is configured to sense cardiac events from the cardiac electrical signal; and
the control module is further configured to:
  determine an estimated rate of the sensed cardiac events during a first operating state of the medical device;
  transition from the first operating state to a second operating state of the medical device when the estimated rate of the sensed cardiac events meets a shockable rate detection criterion;
  set the first signal analysis segment and the second signal analysis segment during the second operating state; and
  remain in the second operating state for a third signal analysis segment after the first signal analysis segment without advancing to a third operating state of the medical device when the TWOS detection criteria are met for the first signal analysis segment.

14. The device of claim 13, wherein:
the sensing module is further configured to:
  receive the cardiac electrical signal by receiving the cardiac electrical signal from a first sensing channel coupled to the plurality of extracardiac electrodes; and
  receive a second cardiac electrical signal from a second sensing channel coupled to the plurality of extracardiac electrodes; and
the control module is further configured to:
  analyze the second cardiac electrical signal for classifying each of a plurality of fourth cardiac signal segments as one of shockable and not shockable; and
  remaining in the second operating state for the third signal analysis segment when the TWOS detection criteria are met for the first signal analysis segment and the plurality of fourth cardiac signal segments are classified as shockable.

15. The device of claim 13, wherein the control module is configured to:
  detect a shockable rhythm when at least the third signal analysis segment is determined to meet shockable rhythm classification criteria and the TWOS detection criteria are not met for the third signal analysis segment;
  advance to the third operating state from the second operating state when the shockable rhythm is detected; and
  charge a capacitor for delivering a shock therapy during the third operating state.

16. An implantable medical device, comprising:
a sensing module configured to receive a cardiac electrical signal via a plurality of extracardiac electrodes coupled to the implantable medical device ; and
a control module coupled to the sensing module and configured to:
  set a first signal analysis segment of the cardiac electrical signal;
  analyze the first signal analysis segment to determine if shockable rhythm classification criteria are met for the first signal analysis segment;
  set a plurality of T-wave oversensing (TWOS) analysis windows;
  analyze cardiac events of the cardiac electrical signal to classify each TWOS analysis window of the plurality of TWOS analysis windows as one of TWOS and no TWOS, each TWOS analysis window being classified as TWOS when cardiac events during the TWOS analysis window satisfy TWOS criteria and classified as no TWOS when the cardiac events during the TWOS analysis window do not satisfy TWOS criteria, wherein the control module is configured to analyze the cardiac events of the cardiac electrical signal by:
    selecting at least one group of at least three consecutive cardiac events from the plurality of cardiac events that are within a given one of the plurality of TWOS analysis windows;
    determining a maximum event amplitude from the at least one group;
    determining an event discrimination threshold using the maximum event amplitude; and
    identifying as R-waves all cardiac events of the plurality of cardiac events within the given one of the plurality of TWOS analysis windows that are equal to or greater than the event discrimination threshold;
    identifying as T-waves all events of the plurality of cardiac events within the given one of the plurality of TWOS analysis windows that have a maximum signal amplitude that is less than the event discrimination threshold; and
    identifying a pattern of TWOS when each one of at least a portion of the identified R-waves is consecutively followed by one of the identified T-waves in an R-T pair;
  determine that TWOS detection criteria are met for the first signal analysis segment when a predetermined number of the plurality of TWOS analysis windows are classified as TWOS; and
  classify the first signal analysis segment as non-shockable in response to determining that the TWOS detection criteria are met.

17. The device of claim 16, wherein the control module is further configured to:
  verify that the R-T pair is a valid R-T pair by verifying at least one of an R-wave amplitude stability, a T-wave amplitude stability, an R-T interval stability and an R-T frequency difference; and
  classify the given signal analysis segment as TWOS when at least two valid R-T pairs within the given signal analysis segment are verified.

18. An implantable medical device, comprising:
a sensing module configured to receive a cardiac electrical signal via a plurality of extracardiac electrodes coupled to the implantable medical device ; and
a control module coupled to the sensing module and configured to:
  set a first signal analysis segment of the cardiac electrical signal;
  analyze the first signal analysis segment to determine if shockable rhythm classification criteria are met for the first signal analysis segment;
  set a plurality of T-wave oversensing (TWOS) analysis windows;
  analyze cardiac events of the cardiac electrical signal to classify each TWOS analysis window of the plurality of TWOS analysis windows as one of TWOS and no TWOS, each TWOS analysis window being classified as TWOS when cardiac events during the TWOS analysis window satisfy TWOS criteria and classified as no TWOS when the cardiac events during the TWOS analysis window do not satisfy TWOS criteria;
  determine that TWOS detection criteria are met for the first signal analysis segment when a predetermined number of the plurality of TWOS analysis windows are classified as TWOS, wherein the control module is configured to determine that the TWOS detection criteria are met for the first signal analysis segment by determining that the TWOS detection criteria are met when a first predetermined number of the plurality of TWOS analysis windows are classified as TWOS and a second predetermined number of the plurality of TWOS analysis windows that are classified as TWOS occur within a third predetermined number of the plurality of TWOS analysis windows preceding the shockable rhythm classification criteria being met; and classify the first signal analysis segment as non-shockable in response to determining that the TWOS detection criteria are met.

* * * * *